(12) United States Patent
Tieu et al.

(10) Patent No.: US 8,535,737 B2
(45) Date of Patent: Sep. 17, 2013

(54) COMPOSITION WITH EXTRACTS FROM OLIVE LEAF, YARROW AND ROSEMARY FOR TREATING HUMAN DISEASES AND CONDITIONS

(71) Applicants: Huu Tieu, Porterville, CA (US); Martin Frederick Loeffler, Porterville, CA (US)

(72) Inventors: Huu Tieu, Porterville, CA (US); Martin Frederick Loeffler, Porterville, CA (US)

( * ) Notice: Subject to any disclaimer, the term of this patent is extended or adjusted under 35 U.S.C. 154(b) by 0 days.

(21) Appl. No.: 13/654,620

(22) Filed: Oct. 18, 2012

(65) Prior Publication Data

US 2013/0101627 A1    Apr. 25, 2013

Related U.S. Application Data

(60) Provisional application No. 61/549,089, filed on Oct. 19, 2011.

(51) Int. Cl.
*A01N 65/00*   (2009.01)
(52) U.S. Cl.
USPC .......................................................... 424/725

(58) Field of Classification Search
None
See application file for complete search history.

(56) References Cited

U.S. PATENT DOCUMENTS

2007/0248693 A1*   10/2007   Mazzio et al. ................ 424/725

* cited by examiner

*Primary Examiner* — Michael Meller

(57) ABSTRACT

The present invention is a medical composition for treating a variety of human diseases and conditions. It comprises an effective amount of Olive Leaf extract, Yarrow extract and Rosemary extract as active components. Its inactive components include *Yucca* extract and *Cassia* Oil. Other inactive components for the purpose of efficient delivery are hereafter identified as "Limonene Concentration Formulation", comprising d-Limonene (C10H16), Glycol EB (2-Butoxyethanol), Calimulse PRS (Benzenesulfonic acid, C10-16-alkyl derivatives, compounds with 2-propanamine), Calsoft L-60 (Benzenesulfonic acid, C10-16-alkyl derivatives, sodium salts, Sodium xylene sulfonate, sodium sulfate), Isopar M Solvent (Light Hydro treated Petroleum Distillates), and Water. This composition can easily enter the circulatory system and quickly reach target tissue and/or organs. Hence it will promote the process of restoring and healing the patient by boosting his or her immune system.

1 Claim, No Drawings

COMPOSITION WITH EXTRACTS FROM OLIVE LEAF, YARROW AND ROSEMARY FOR TREATING HUMAN DISEASES AND CONDITIONS

The current application claims a priority to the U.S. Provisional Patent application Ser. No. 61/549,089 filed on Oct. 19, 2011.

FIELD OF THE INVENTION

The present invention relates to a medical composition for the purpose of treating human diseases and other medical conditions. More particularly, the invention relates to a composition comprising active components from certain natural plant extracts, such as Olive Leaf extract, Yarrow extract and Rosemary extract; inactive components such as *Yucca* extract and *Cassia* Oil. This composition functions to treat various human diseases and conditions, including, but not limited to, cancer, cardiovascular diseases, herpes, infections, AIDS, asthma, Alzheimer disease, inflammatory conditions, urinary problems, hair growth problems, serious or life-threatening and other conditions. Even more particularly, the present invention relates to a composition that further includes a delivery system which can quickly and efficiently deliver the medically effective components to the target of the body for treatment.

BACKGROUND OF THE INVENTION

The use of natural plants or plant extracts as medicines has a long history that even predates the written human records. Many of the pharmaceuticals currently available to physicians have a long history of use as herbal remedies, such as opium, aspirin, digitalis, and quinine. The World Health Organization (WHO) estimates that 80 percent of the populations of some Asian and African countries presently use herbal medicine for some aspect of primary health care. Studies in the United States and Europe have shown that their use is less common in clinical settings in these countries; but has become increasingly more in recent years as scientific evidence about the effectiveness of herbal medicine has become more widely available. Herbal remedies are seen by some as a natural treatment to be preferred to those synthetic medical compounds that have been industrially produced. A survey released in May 2004 by the National Center for Complementary and Alternative Medicine focused on who used complementary and alternative medicines (CAM) in the United States. According to this survey, herbal therapy, or use of natural products was the most commonly used CAM therapy (18.9%). Herbal remedies are also very common in Europe. For instance, in Germany, herbal medications are dispensed by apothecaries; and prescription drugs are sold alongside essential oils, herbal extracts, or herbal teas.

For the medicinal purpose, compared with modern pharmaceuticals that are usually chemically synthesized, the natural herbs and plants have certain major advantages. Nowadays, it is universally agreed that those pharmaceuticals are prohibitively expensive for most people. In comparison, herbal medicines usually cost much less, partially because that they can be grown from seeds or gathered from nature for little or even no cost. The significance of a medicine resides in its availability for most of the patients who need it. A medicine that only the wealthy can afford has much less benefit for the entire society. On the other hand, natural herbs are usually safer than most of the chemically synthesized modern pharmaceuticals. They generally have little side effects and are not invasive. Many of the medicinal herbs or plants are actually spices or foods that people consume in everyday lives.

With these advantages, many persons are currently investigating the potential of treating a variety of human diseases and other conditions with more natural and/or herbal compounds or compositions to reduce the side effects and inefficiencies associated with treating patients with conventional synthetic drugs. For instances, a typical cancer treatment comprises the use of radiation therapy and chemotherapy, which are known to both be invasive and with a variety of debilitating effects on the patient. Diseases such as HIV/AIDS are primarily treated by anti-viral cocktails that are generally considered somewhat experimental, palliative and with serious side effects. Diabetes, both type I and II, are typically treated with invasive insulin injection or Sulfonylurea pills. Other diseases, including Alzheimer's, Parkinson's, Cerebral Palsy, Dermatomyositis and Systemic Lupus have no known cure and/or known effective treatment. Due to the problems associated with current available drugs and treatments or the lack of drugs and treatments, there is a huge need to identify medicinally effective compounds or compositions from natural herbs and plants to treat various diseases and conditions.

Plants have the ability to synthesize a wide variety of chemical compounds that are used to perform important biological functions, and to defend against attack from predators such as insects, fungi and herbivorous mammals. Many of these phytochemicals have medicinal efficacy for treating human diseases and conditions, or have beneficial effects on long-term health, when consumed by humans. At least 12,000 such compounds or compositions have been isolated so far for this purpose. However, this number is estimated to be less than 10% of the total available in nature according to many current studies. Therefore, developing new medicinal compositions from natural herbs and plants has big commercial potential and huge health benefits to the society.

In the present invention, three medicinally active components have been incorporated in a newly-developed medical composition for the purpose of treating various human diseases and conditions. They are Olive Leaf extract, Yarrow extract and Rosemary extract.

Olive tree (*Olea europaea*), a small evergreen native to Mediterranean regions, has been revered throughout history for its contribution to the culinary and healing arts. Its extracts have been used as a folk remedy for treating a variety of infections, wounds, fevers, as well as for skin rashes and boils. Olive Leaf is the leaf of the Olive tree. While Olive oil is well known for its flavor and health benefits, the leaf has been used medicinally in various times and places. Natural Olive Leaf and Olive Leaf extracts are now marketed as an anti-aging, an immunostimulator and an antibiotic. Clinical evidence has also proven its effect to reduce blood pressure. Bioassays support its antibacterial, antifungal, and anti-inflammatory effects at a laboratory level. A liquid extract made directly from fresh Olive leaves has recently gained international attention when it was shown to have an almost double antioxidant capacity than that in green tea extract, and about 400% higher than that in Vitamin C. Olive Leaf harbors the antioxidant properties that help protect the body from the damage resulted from continuous activity of free radicals. Free radicals are highly reactive chemical substances that, when oxidized, can cause cellular damage if left unchecked. Some recent researches on Olive Leaf has shown its antioxidants to be effective in treating some tumors and cancers, such as liver, prostate, colon, skin and breast cancers. It has also been identified that olive leaf is usually associated with a lower risk of coronary heart disease. The primary medically active constituents in unprocessed Olive Leaf are believed to be the antioxidants of oleuropein and hydroxytyrosol, as well as several other polyphenols and flavonoids, including oleocanthal. Olive Leaf itself can be taken as a liquid concentrate, dried leaf tea, powder, or capsule. The leaf extracts can be made in powder, liquid concentrate, or capsule form. Recently, the fresh-picked leaf extracts are quickly gaining popularity due to the broader range of healing components they contain.

Yarrow (*Achillea millefolium*) is a flowering plant in the Asteraceae family. The genus name *Achillea* is derived from mythical Greek character, Achilles, who reportedly carried it with his army to treat battle wounds. It is native to the northern hemisphere. In New Mexico and southern Colorado, it is called plumajillo, or "little feather", for the shape of its leaves. In antiquity, Yarrow was already known as Herbal Militaris (military herb), for its use in staunching the flow of blood from wounds. Other common names for this species include common Yarrow, gordaldo, nosebleed plant, old man's pepper, devil's nettle, sanguinary, milfoil, soldier's woundwort, thousand-leaf (as its binomial name affirms), and thousand-seal. Yarrow is an erect herbaceous perennial plant that produces one to several stems 0.2 m to 1 m tall and with a rhizomatous growth form. Leaves are evenly distributed along the stem, with the leaves near the middle and bottom of the stem being the largest. The leaves have varying degrees of hairiness (pubescence). The leaves are 5 cm to 20 cm long, bipinnate or tripinnate, almost feathery, and arranged spirally on the stems. The leaves are cauline and more or less clasping. There are generally 3 to 8 ray flowers that are ovate to round. Yarrow is frequently found in the mildly disturbed soil of grasslands and open forests. The plant has a strong, sweet scent, similar to chrysanthemums. The herb is purported to be a diaphoretic, astringent, tonics, stimulant and mild aromatic. It contains isovaleric acid, salicylic acid, asparagines, sterols, flavonoids, bitters, tannins and coumarins. The plant has a long history as a powerful "healing herb" used topically for wounds, cuts and abrasions. This medicinal action is also reflected in some of the common names mentioned below, such as staunch weed and Soldier's Woundwort. In addition, yarrow has also been used as a food.

Rosemary (*Rosmarinus officinalis*) is native to the Mediterranean; but now grows throughout much of the temperate regions in Europe and America. Rosemary thrives in chalky or sandy soil in full sun. The herb grows well on dry, rocky slopes near the sea. Its name is derived from the Latin ros marinus, meaning "sea dew." Other common names for the herb include polar plant, compass-weed, or compass plant. The specific name, officinalis, refers to the herb's inclusion in official Western listings of medicinal herbs. Rosemary has been a prized seasoning and natural medicine for thousands of years. Part of Rosemary's popularity came from the widespread belief that rosemary stimulated and strengthened the memory; a quality for which it is still traditionally used. Legend abounds around this lovely perennial known as the "herb of remembrance." Rosemary oil was first extracted in the 14th century, after which it was used to make Queen of Hungary water, a very popular cosmetic used at that time. In the 16th and 17th centuries, Rosemary became popular as a digestive aid in apothecaries. Recently, as modern research focuses on the beneficial active components in Rosemary, the appreciation for this herb's therapeutic as well as culinary value has been renewed. Rosemary has been used to stimulate circulation and to alleviate blood pressure problems. One of the constituents in this plant is rosmarinic acid, known to be a powerful antioxidant. In addition, Rosemary extract has been shown to have anticancer properties. Oil of Rosemary has effective antibacterial and antifungal properties. It is often used as an astringent due to its high levels of tannins. The tannins also allow Rosemary to be used to shrink swollen mucous membranes. When applied topically as a tincture it will alleviate joint pain and arthritis. Rosemary is also purported to have gastrointestinal influences as it helps fat digestion, relieves gas, and is thought to aide with diarrhea. Other uses include hair tonics as it helps to reduce dandruff, which is supposed to be wonderful for dark haired women, and provides shine to dull hair.

In addition to the above active components, the newly-developed medical composition also contains certain inactive components, such as *Yucca* extract and *Cassia* oil.

*Yucca* plants include a number of different trees and shrubs found in aid portions of North and Central America. Common species include *Yucca aloifolia* (Spanish bayonet), *Yucca brevifolia* (Joshua tree), *Yucca filamentossa* (Adam's needle), *Yucca glauca* (soap-weed), and many others. All parts of the plant, as well as many different species, are widely used. *Yucca* extract is used as a dietary supplement in the United States; and is commonly marketed as an anti-inflammatory herb, primary for the treatment of arthritis symptoms. There are also claims that *Yucca* may help reduce blood pressure and cholesterol levels. Traditionally *Yucca* has been used in different cultures for a wide variety of medical conditions, including gout, gall bladder problems, diabetes, genitourinary disorders, indigestion, and constipation, and also been used as a diuretic and used topically for inflammation or for general skin cleansing. Native Americans have created soap, shampoo, rope, and textiles from *Yucca* plants. Its plant constituents are also used commercially as foaming agents and flavorings. *Yucca* plant contains steroidal saponins such as sarsasapogenin and tigogenin. Saponins are widely used for their detergent and foaming properties; and have also been studied in animals for their potential anti-cholesterol, anti-inflammatory, and anti-carcinogenic activities. *Yucca* leaf proteins interfere with protein synthesis in cells infected by herpes simplex virus and cytomegalovirus. Flowers of certain *Yucca* species contain polysaccharides with tumor-inhibiting effects in mice. Saponins may cause dose-dependent gastrointestinal distress, especially in raw plant form. In controlled clinical trials using *Yucca* tablets, mild and transient complaints were reported in about 9% patients, and unfavorable gastrointestinal effects were reported in about 4%. Native Americans and others have used the *Yucca* plant as food for centuries without any known adverse effects. Precise doses for *Yucca* have not been established. In the clinical studies that used a *Yucca* saponin extract, tablets were taken three times daily, usually with or after meals.

*Cassia* or Cinnamon is an evergreen native to southern China, Bangladesh, Uganda, India, and Vietnam. In the United States of America, cassia is often sold under the culinary name of "cinnamon". The buds are also used as a spice, especially in India, and were once used by the ancient Romans. Whole branches and small trees are harvested for cassia bark, unlike the small shoots used in the production of cinnamon; this gives cassia bark a much thicker and rougher texture than that of true cinnamon. Most of the spice sold as cinnamon in the United States and Canada is actually *cassia*. In some cases, cassia is labeled "Chinese cinnamon" to distinguish it from the more expensive Ceylon cinnamon (*C. verum*), which is the preferred form of the spice used in Mexico, Europe and Oceania. *Cinnamomum aromaticum* is produced in both China and Vietnam. Until the 1960s, Vietnam was the world's most important producer of Saigon cinnamon (*C. loureiroi*), a species which has higher oil content than *cassia*, and consequently has a stronger flavor.

Saigon cinnamon is so closely related to cassia that it was often marketed as cassia (or, in North America, "cinnamon"). Among the three forms of *cassia*, it is the form which commands the highest price. *Cassia* has a strong and sweet flavor, similar to Saigon cinnamon, although the oil content is lower. *Cassia* buds, although rare, are also occasionally used as a spice. They resemble cloves in appearance and have a mild, flowery cinnamon flavor. *Cassia* buds are primarily used in old-fashioned pickling recipes, marinades, and teas.

The "Limonene Concentration Formulation" delivery system is identified as the following: Formulation Compound as Delivery System for Use in Pharmaceutical and Agricultural Products (U.S. Provisional Application 61495987 and 61549188). It comprises d-Limonene (C10H16), Glycol EB (2-Butoxyethanol), Calimulse PRS (Benzenesulfonic acid, C10-16-alkyl derivatives, compounds with 2-propanamine), Calsoft L-60 (Benzenesulfonic acid, C10-16-alkyl derivatives, sodium salts, Sodium xylene sulfonate, sodium sulfate), Isopar M Solvent (Light Hydro treated Petroleum Distillates), and water ($H_2O$).

The component d-Limonene has been around for many years and has been proven to be safe for use with plants, animals and humans. This chemical is a major constituent of citrus oils, including those obtained from orange, lemon, lime and grapefruit, extracted from citrus rinds or peels. During the processing of citrus fruits into juice, the citrus oil is pressed out of the rind. This citrus oil is next separated from juice and then distilled to produce certain flavor and fragrance compounds. The bulk of the oil, however, is left behind and collected, which contains food grade d-Limonene. After juicing process, the rinds are conveyed to a steam extractor to extract more oil from the rind. The steam is condensed, a layer of citrus oil floats on the surface of the condensed water, providing technical grade d-Limonene. It is well known that, as a safe chemical, d-Limonene can be utilized along with other chemicals to make certain compositions which are effective as a fungicide, bactericide, adjuvant, or in other pharmaceutical and agricultural applications. For instances, in U.S. Pat. No. 3,023,144 to Graethouse, et al., it described certain d-Limonene-based compounds being configured as topical agents for human and animal use, in the forms of ointments, lotions, creams, shampoos or similar products. In U.S. Pat. No. 3,960,539 to Newhall, it disclosed a d-Limonene use in a composition for the regulation of plant growth and the control of nematodes and fungi on plants. In U.S. Pat. No. 4,379,168 to Dotolo, it described the use of d-Limonene in a pesticide composition that also contains a surfactant or emulsifier in water to form a composition that is non-toxic and no-irritating to animals. In U.S. Pat. No. 6,849,276 to Dufau, et al. it disclosed a liquid composition having a monocyclic terpenic hydrocarbon, such as d-Limonene, that has fungicidal, bactericidal and bacteriostatic activities with the copper maintained in suspension in the aqueous emulsion.

Butyl Glycol EB (2-Butoxyethanol) is an organic solvent with the formula C6H14O2. The chemical is a colorless liquid with a sweet, ether-like odor. It is butyl ether of ethylene glycol. The main use of 2-Butoxyethanol is as a solvent in paints and surface coatings, followed by in cleaning products and inks. Other products which contain 2-Butoxyethanol include acrylic resin formulation, asphalt release agents, firefighting foam, leather protectors, oil spill dispersants, bowling pin and lane degreaser, and photographic strip solutions. 2-Butoxyethanol is a primary ingredient of various whiteboard cleaners, liquid soaps, cosmetics, dry cleaning solutions, lacquers, varnishes, latex paints, agricultural products, and pharmaceuticals. It also appears to be excellent at killing most insects and arachnids. The chemical 2-Butoxyethanol usually decomposes in the environment within a few days and not been identified as a major environmental contaminant. It is not known to build up in any plant or animal species.

CALIMULSE® PRS is produced by using a proprietary sulfonation process to ensure its consistency, uniformity and high purity, which makes it an excellent emulsifier for use in a long list of products for degreasing surfaces, promoting latex emulsification, dry cleaning, improving pigment dispersion, spreading qualities in latex paints; as oil-slick emulsifiers, or used in the oil field to enhance oil recovery, or in other pharmaceutical applications. CALIMULSE® PRS is an excellent highly active degreaser, wetting agent and detergent. Its applications also include HI&I Biodegradable which was approved under the regulation CFR21.

CALSOFT® L-60 is also an emulsifier with high purity, which makes it an excellent emulsifier for use in all-purpose cleaners, detergents, degreasers, agricultural products, pharmaceuticals and other emulsifying agents. Manufactured by various producers using a proprietary sulfonation process; CALSOFT® L-60 is biodegradable, dependable, uniform, high purity and low in color; ensuring a quality performance. CALSOFT® L-60 is available in free-flowing dry material, paste liquid and various salt forms. CALSOFT® L-60 in the U.S. is an EPA and DFE approved product and listed as a clean ingredient.

ISOPAR® M solvent is a clear Isoparaffin fluid, typically with less than 1 ppm benzene and less than 1 ppm sulphur. ISOPAR® M fluids are high-purity synthetic isoparaffins with consistent and uniform quality. They are produced at manufacturing facilities complying with Good Laboratory Practice. It delivers one of the narrowest boiling ranges for any hydrocarbon fluid. The high purity of ISOPAR® M, along with an array of other technical attributes, offers significant benefits for both industrial processes and pharmaceutical and agricultural applications.

Water is the chemical substance with chemical formula $H_2O$. One molecule of water has two hydrogen atoms covalently bonded to a single oxygen atom. Water appears in nature in all three common states of matter and many different forms on earth. Water is widely used in many chemical reactions as a solvent or a reactant, but also less commonly used as a solute or catalyst. In inorganic reactions, water is a common solvent, dissolving many ionic compounds. In organic reactions, it is not usually used as a reaction solvent, because it does not dissolve the reactants well and is amphoteric (acidic and basic) and nucleophilic. Nevertheless, these properties are sometimes desirable.

The immune system in the human body is known to be able to resist many types of diseases, and "treat" diseases and other medical conditions without the addition of many of the medicines that are commonly used and prescribed today. In many cases, however, for a variety of reasons, a person's immune system is weakened or otherwise unable to effectively respond to an attack against the body during a diseases or other medical condition. What is needed therefore is a medical composition to boost a person's immune system. So his or her body can be more effectively responding and resisting the diseases or medical conditions. This newly-developed composition in the present application can help to treat a variety of diseases and medical conditions by boosting a person's own immune system. Preferably, the claimed composition would be safe to use with very few, if any, side effects. The composition includes an effective delivery system that directs the active components to travel to the target site in the body for a more efficient treatment.

SUMMARY OF THE INVENTION

Based on the foregoing, one aspect of the invention is to provide a medical composition, which includes active components of Olive Leaf extract, Yarrow extract and Rosemary extract, along with inactive components of *Yucca* extract and *Cassia* Oil, to treat human diseases and conditions. The present invention provides many treatment benefits, along with avoiding many problems associated with conventional treatments. The composition in the present invention can effectively and safely boost a person's immune system; so his or her body will be more effectively responding and resisting to the diseases or medical conditions. The claimed composition has no known side effects. It will thereby eliminate the need for a secondary or supplemental medication to address the side effects resulted from many conventional medications.

On another aspect of the present invention, in addition to Olive Leaf extract, Yarrow extract and Rosemary extract, along with various inert components, this composition also comprises an effective delivery system, which helps to quickly deliver the active components to the target tissue or organ in the body. In the present invention, this delivery system can be Limonene Concentration Formulation that comprises d-Limonene (C10H16), Glycol EB (2-Butoxyethanol), Calimulse PRS (Benzenesulfonic acid, C10-16-alkyl derivatives, compounds with 2-propanamine), Calsoft L-60 (Benzenesulfonic acid, C10-16-alkyl derivatives, sodium salts, Sodium xylene sulfonate, sodium sulfate), Isopar M Solvent (Light Hydro treated Petroleum Distillates), and Water.

In a preferred usage, this composition will be administered orally, preferably sublingually, which would eliminate the need of utilizing invasive administration techniques. In the above preferred embodiment comprising a unique and effective delivery system, Limonene Concentration Formulation, which allows the active components to readily enter the human body's circulatory system, and quickly reach the target area where the treatment is needed. Because the composition of the present invention is readily penetrating through the Blood Brain Barrier, it may accomplish the objective of restoring and healing the patient in a very short period time for those diseases related to the central nervous system.

One primary objective of the present invention is to provide a medical composition for treating various human diseases and medical conditions. It offers the advantages of treating the diseases and conditions mentioned previously. It functions to boost a person's immune system. So his or her body can more effectively resist and respond to the diseases or medical conditions.

DETAILED DESCRIPTION OF THE INVENTION

With reference to the various preferred embodiments of the present invention set forth below, these embodiments are intended to be representative of one or more ways of configuring the medical composition of the present invention. Although specific chemical, materials, configurations and uses are set forth herein, it should be understood that a number of variations to the components described herein can be made without changing the scope and function of the present invention. For instance, although the description provided herein sets forth certain components and percentages of those components that make up the preferred embodiments of the medical composition of the present invention, those who are skilled in the art will readily understand that this is merely for purposes of simplifying the present disclosure and that the present invention is not so limited. Specifically, as will be readily appreciated by those skilled in the art, various equivalent chemicals can be utilized to make up the medical composition of the present invention.

Provided is a medical composition for treating human disease and medical conditions, which comprises certain natural herb or plant extracts as active components, along with some inactive components including *Yucca* extract and *Cassia* Oil. In a preferred embodiment, the medical composition of the present invention comprises medically effective amount of Olive Leaf extract, Yarrow extract and Rosemary extract as the active components. In order to allow them to be uniquely identified, the CAS registry numbers are provided below for each of the components. The CAS Registry Numbers are unique numerical identifiers assigned by the Chemical Abstracts Service to every chemical described in the open scientific literature (currently including those described from at least 1957 through the present) and including elements, isotopes, organic and inorganic compounds, ions, organometallics, metals, and nonstructurable materials. Olive Leaf extract is identified as CAS No. 32619-42-4; Yarrow-65 extract, CAS No. 84082-83-7; and Rosemary-55 extract, CAS No. 84604-14-8. They are available from EDM Industries Company located in Strathmore, Calif.

In another embodiment, this composition further contains an effective delivery system, comprising d-Limonene (CAS No. 8028-48-6), an organic solvent, as well as one or more inert solvents and inert emulsifiers. With regard to the these medically inactive components, the d-Limonene (CAS No.: 8028-48-6) is available from Florida Chemical Company in Winter Haven, Fla.; Glycol EB 2-Butoxyethanol (CAS No. 111-76-2) available from Univar Corporation in Seattle, Wash.; Isopar M (CAS No. 64742-47-8) available from Exxon-Mobile Corporation in Fairfax, Va. Other fluid inert solvents, the Calimulse PRS (CAS No. 68584-24-7, 68584-87-3 and 7732-18-5) and Calsoft L-60 (CAS No. 68081-81-2, 68648-87-3, 1300-72-7 and 7757-82-6) are available from Pilot Chemical Company in Cincinnati, Ohio. Other inert components are comprised of *Yucca*-X70 *Yucca* extract (CAS No. 90147-57-2), which is available from Cell-U-Con in Strathmore, Calif.; and *Cassia* Oil (CAS No. 8007-80-5) is available from Reagent World Incorporation in Ontario, Calif.

A preferred embodiment of the medical composition in the present invention is set forth in the formulation table below:

| Chemical | Approximate (%) By Volume Referred Range | Use |
| --- | --- | --- |
| Olive Leaf extract | 10.00-18.00 | Active |
| Yarrow-65 extract | 8.00-15.00 | Active |
| Rosemary-55 extract | 13.00-20.00 | Active |
| d-Limonene | 14.00-20.00 | Solvent |
| 2-Butoxyehtnaol | 11.00-18.00 | Solvent |
| Isoparaffinic Hydrocarbon | 5.00-10.00 | Solvent |
| Benzenesulfonic acid, $C_{10}$-$_{16}$-alkyl derivatives, (sodium or 2-propanamine salt) | 15.00-30.00 | Emulsifier |
| Water | 5.00-15.00 | Solvent |
| Yucca-X70 extract | 4.00-7.00 | Adjuvant |
| Cassia Oil | 0.50-2.00 | Solvent |

This unique delivery system of the medical composition in present invention is substantially responsible for the health benefits of the medical composition. It allows the active components in the composition to reach circulatory system in a chemically unchanged form. As a result, the claimed medical composition has a bioavailability of nearly 100%. The three active components in the medical composition, namely Olive Leaf extract, Yarrow extract and Rosemary extract, show bio-equivalence and therapeutic equivalence.

In another embodiment, the medical composition is prepared in an oral liquid or a gel capsule form that is administered to the patient by mouth, preferably sublingually, utilizing liquid drops. The medical composition reaches the circulatory system very rapidly, nearly instantaneously, bypassing the so called "First Pass Hepatic Metabolism" effect. Additionally, this medical composition has the capability to cross the "Blood-Brain Barrier," thereby benefiting certain neurological conditions.

The medical composition of the present invention accomplishes its objective of beneficially treating various human diseases and conditions by repairing, restoring and healing the damaged (such as damaged by free radicals) tissue and organs, which is achieved through the extraordinary delivery system of the medical composition. The beneficial effects of the medical composition start to act on the damaged tissue and organs as soon as it reaches the target area. After the medical composition has already functioned on the disease or medical condition, it is anticipated that a maintenance amount of the medical composition will be necessary for continued health benefits.

The medical composition of the present invention can stimulate the generation of stem cells in the body. These stem cells include Hematopoietic, stromic and mesenchymal stem cells that can differentially initiate and induce pluripotency throughout the various active systems of the body including but not limited to circulatory, respiratory and central nervous systems. The composition increases the generation of stem cells, as well as the regeneration of damaged tissue in the body resulting from a disease or medical condition. Additionally, it also helps to boost blood flow through the capillaries. Furthermore, this medical composition is a highly mobile regent in the body; and has been shown functioning as a general inhibitor for bactericidal, viral, inflammatory, neoplastic, and autoimmune diseases.

As an immune system booster, the medical composition of the present invention has several immediate and intermediate benefits as well as several observed therapeutic properties. The immediate stimulant benefits include an increase in energy, alertness and appetite, improved restful sleep and bowel regulation. The intermediate benefits realized by the medical composition include improved general well-being, reduction in anxiety, psychosis and memory loss, as well as improved socialization. In general, this medical composition of the present invention has the following observed beneficial effects: anti-neoplastic, anti-inflammatory, anti-oxidant, anti-bacterial, anti-fungal, anti-parasitic, anti-viral and analgesic. A genotoxicity study has also been applied to confirm the safety of the composition.

The medical composition of the present invention is manufactured by mixing them in order, beginning with d-Limonene, and next Calimulse PRS Isopropyl amine, Sodium dodecylbenzene Sulfonate, Calsoft L-60 Benzene Sulfonic acid, Butyl Cellusolve (EB) 2-Butoxyethanol, Isopar M Isoparaffinic Hydrocarbon, Olive Leaf extract, Yarrow extract (Yarrow-4), Rosemary extract (Rosemary-2), *Yucca*-X70 (*Yucca* extract) and *Cassia* Oil. The first three components must be added in the order set forth at about at 65° F. or above to prevent the separation of the composition. Olive Leaf extract is added only after the "Limonene Concentrate Formulation" is complete and tested for good quality characteristics. All ingredients in this product are tech grade. There is no reaction occurs when in-process components are being formulated. The later-occurred impurities in the composition will be removed and further verified by a bath test, or in a test conducted at three months intervals. The medical composition of the present invention should be manufactured utilizing established current Good Manufacturing Practices. The physical and chemical properties of the medical product include a dark brown liquid form with citrus and cinnamon type fragrance, a taste that is tangy and mildly bitter, being suitable for room temperature storage and has a shelf-life of approximately one year after the manufacturing date. The inherent beneficial properties of the medical composition are achieved with a natural (non-synthetic) product that is ubiquitous in nature. The benefits of the medical composition of the present invention are applicable to pediatric, adult and geriatric patients. In one embodiment, the medical composition is taken through oral administration. In the case when the patient has a sensitivity of the mouth and/or throat, then an administration orally mixed solution of one teaspoon of yogurt may be used, or the pure solution may be giving preferably by applying 0.25 ml to 0.50 ml drops of the liquid solution under the tongue, this is advisable one to five times a day.

While there are shown and described herein specific forms of the invention, it will be readily apparent to those skilled in the art that the invention is not so limited, but is susceptible to various modifications and rearrangements in materials without departing from the spirit and scope of the present invention. In particular, it should be noted that the present invention is subject to modification with regard to any the combination of materials and the prescribed use of the medical composition. For instance, there are numerous components described herein that can be replaced with equivalent functioning components to accomplish the objectives of the present invention.

What is claimed is:

1. A pharmaceutical composition for treating cancer consisting essentially of therapeutically effective amounts of yucca extract, cassia oil, olive leaf extract, yarrow extract and rosemary extract.

* * * * *